（12） United States Patent
Ogden et al.

(10) Patent No.: US 6,368,292 B1
(45) Date of Patent: Apr. 9, 2002

(54) METHOD FOR USING ACOUSTIC SHOCK WAVES IN THE TREATMENT OF MEDICAL CONDITIONS

(75) Inventors: John A. Ogden, Atlanta; John F. Warlick, Woodstock, both of GA (US)

(73) Assignee: Healthtronics Inc., Marietta, GA (US)

( * ) Notice: Subject to any disclaimer, the term of this patent is extended or adjusted under 35 U.S.C. 154(b) by 0 days.

(21) Appl. No.: 09/471,057

(22) Filed: Dec. 22, 1999

Related U.S. Application Data

(60) Continuation-in-part of application No. 09/342,151, filed on Jun. 25, 1999, which is a continuation-in-part of application No. 09/120,267, filed on Jul. 21, 1998, which is a continuation-in-part of application No. 08/799,585, filed on Feb. 12, 1997, now abandoned, application No. 09/471,057, which is a continuation-in-part of application No. 09/427,686, filed on Dec. 23, 1998, which is a division of application No. 08/799,585, filed on Feb. 12, 1997, now abandoned.

(51) Int. Cl.[7] .................................. A61N 7/00
(52) U.S. Cl. ........................... 601/2; 600/427
(58) Field of Search ..................... 601/2–4; 600/427, 600/439; 128/898

(56) References Cited

U.S. PATENT DOCUMENTS

| | | | |
|---|---|---|---|
| 2,559,227 A | 7/1951 | Rieber | 128/24 |
| 3,942,531 A | 3/1976 | Hoff et al. | 128/328 |
| 4,530,360 A | 7/1985 | Duarte | 128/419 |

(List continued on next page.)

FOREIGN PATENT DOCUMENTS

| | | |
|---|---|---|
| DE | 4036981 | 5/1992 |
| DE | 19718513 | 5/1998 |
| DE | 19718512 | 6/1998 |
| EP | 0324163 | 7/1989 |
| EP | 0450423 | 1/1997 |
| WO | WO 96/09621 | 3/1996 |

OTHER PUBLICATIONS

Dahmen, G.P., et al., "Extracorporeal Shock Wave Therapy (ESWT) in the Bone–Adjacent Soft Tissue Region of the Shoulder," *extracta Orthopaedica*, vol. 15, No. 11 (1992).

Final Programme and Abstracts from European Society for Musuloskeletal Shockwave Therapy, London, England, May 27–29, 1999 pp. 1–65.

Lin, Jian–Hao et al., "Temporal expression of nitric oxide synthase isoforms in healing Achilles tendon," *Journal of Orthopaedic Research*, No. 19 (2001), pp. 136–142.

*Primary Examiner*—Ruth S. Smith
(74) *Attorney, Agent, or Firm*—Kilpatrick Stockton LLP

(57) ABSTRACT

This invention relates to methods for medical treatment of pathological conditions. More particularly, the invention relates to methods for using acoustic shock waves to treat a variety of pathological conditions such as plantar warts, deep bone bruises, prostate cancer, benign prostatic hypertrophy, urinary incontinence, and spinal cord injuries, including the reduction or removal of scar tissue to aid in spinal cord regrowth.

8 Claims, 2 Drawing Sheets

U.S. PATENT DOCUMENTS

| | | |
|---|---|---|
| 4,669,472 A | 6/1987 | Eisenmenger ................ 128/328 |
| 4,887,600 A | 12/1989 | Watson et al. ............... 606/128 |
| 4,896,673 A | 1/1990 | Rose et al. ............ 128/660.03 |
| 4,905,671 A | 3/1990 | Senge et al. .................. 128/24 |
| 4,979,501 A | 12/1990 | Valchanov et al. ............ 128/24 |
| 5,071,422 A | 12/1991 | Watson et al. ............... 606/128 |
| 5,172,692 A | 12/1992 | Kulow et al. .................. 128/24 |
| 5,176,675 A | 1/1993 | Watson et al. ................ 606/15 |
| 5,178,135 A | 1/1993 | Uchiyama et al. .......... 128/240 |
| 5,191,880 A | 3/1993 | McLeod et al. ............... 128/24 |
| 5,211,160 A | 5/1993 | Talish et al. ................... 128/24 |
| 5,259,384 A | 11/1993 | Kaufman et al. ......... 128/660.1 |
| 5,284,143 A | 2/1994 | Rattner .................... 128/653.1 |
| 5,309,898 A | 5/1994 | Kaufman et al. ............... 601/2 |
| 5,316,000 A | 5/1994 | Chapelon et al. ...... 128/660.03 |
| 5,327,890 A | 7/1994 | Matura et al. ........... 128/653.1 |
| 5,374,236 A | 12/1994 | Hassler ........................... 601/2 |
| 5,393,296 A | 2/1995 | Rattner .......................... 601/2 |
| 5,409,446 A | 4/1995 | Rattner .......................... 601/4 |
| 5,419,327 A | 5/1995 | Rohwedder et al. .... 128/660.03 |
| 5,458,130 A | 10/1995 | Kaufman et al. ....... 128/661.01 |
| 5,458,652 A | 10/1995 | Uebelacker .................... 601/4 |
| 5,524,620 A * | 6/1996 | Rosenschein .................. 601/2 |
| 5,545,124 A | 8/1996 | Krause et al. .................. 601/2 |
| 5,595,178 A | 1/1997 | Voss et al. ................ 128/653.1 |
| 5,692,509 A | 12/1997 | Voss et al. ................ 128/653.1 |
| 6,186,963 B1 * | 2/2001 | Schwarze et al. .............. 601/2 |
| 6,190,336 B1 * | 2/2001 | Duarte et al. ................... 601/2 |

* cited by examiner

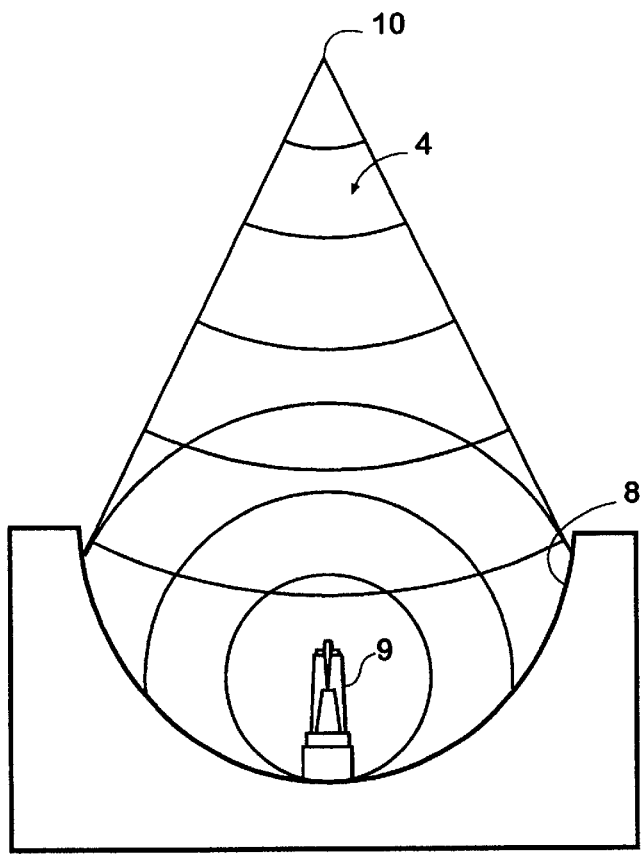
FIG.1
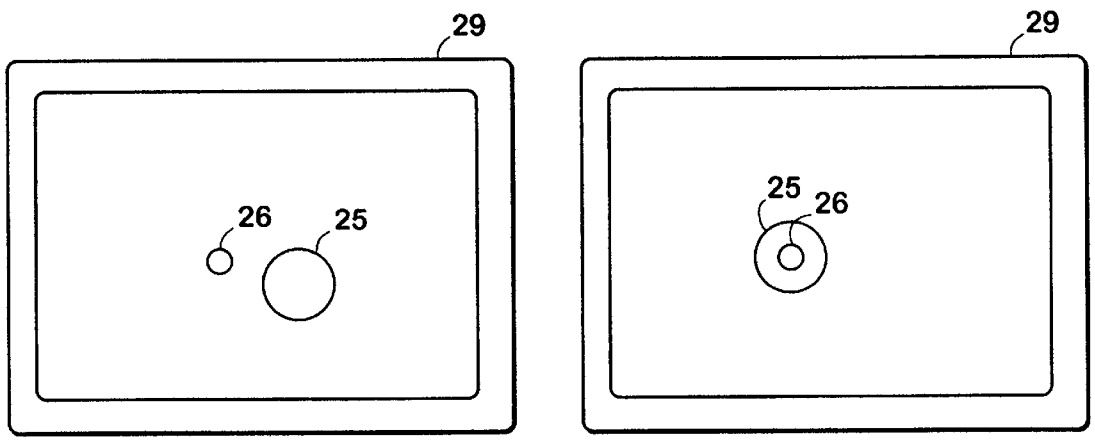
FIG.4 FIG.5

METHOD FOR USING ACOUSTIC SHOCK WAVES IN THE TREATMENT OF MEDICAL CONDITIONS

CROSS-REFERENCE TO RELATED APPLICATIONS

This application is a continuation-in-part of U.S. application Ser. No. 09/342,151, filed Jun. 25, 1999, now pending, which is a continuation-in-part of (1) U.S. application Ser. No. 09/120,267, now abandoned, filed Jul. 21, 1998, which is a continuation-in-part of U.S. application Ser. No. 08/799,585, now abandoned, filed Feb. 12, 1997, and of (2) U.S. application Ser. No. 09/427,686, now pending, filed Dec. 23, 1998, which is a divisional of U.S. application Ser. No. 08/799,585, now abandoned, filed Feb. 12, 1997, the entire contents of each of which are hereby incorporated by reference.

BACKGROUND OF THE INVENTION

1. Field of the Invention

This invention relates to methods for medical treatment of pathological conditions. More particularly, the invention relates to methods for using acoustic shock waves to treat a variety of pathological conditions.

2. Description of Related Art

The use of energy wave forms for medical treatment of various bone pathologies is known in the art. For example, U.S. Pat. No. 4,530,360, issued on Jul. 23, 1985 to Duarte, teaches the use of ultrasound transducers, in direct contact with the skin of the patient, for transmitting ultrasound pulses to the site of the bone defect. Duarte teaches a nominal ultrasound frequency of 1.3 to 2.0 MHz, a pulse width range of 10 to 2000 microseconds, and a pulse rate varying between 100 and 1000 Hz Duarte maintains the ultrasound power level below 100 milliwatts per square centimeter, with treatments lasting no more than 20 minutes per day. Other devices utilize piezoelectric materials fastened adjacent to the pathological site on the patient's limb to produce ultrasonic energy in the vicinity of the bone pathology for administering therapy. Examples of such prior art references include U.S. Pat. Nos. 5,211,160, 5,259,384, and 5,309,898.

Clinicians have also utilized shock waves to treat various pathologies. Early approaches of using shock waves for medical treatment required immersing the patient in water and directing a shock wave, generated by an underwater spark discharge, at a solid site to be treated, such as a bone or kidney stone. When the shock wave hits the solid site, a liberation of energy from the change of acoustic impedance from water to the solid site produces pressure in the immediate vicinity of the site. For example, U.S. Pat. No. 4,905,671 to Senge et al., issued on Mar. 6, 1990, teaches a method applying acoustic shock waves to induce bone formation. Senge et al. teaches that the acoustical sound waves utilized by Duarte (and similar references) for treatment of bone have a generally damped sinusoidal wave form centered on ambient pressure. More specifically, Senge et al. teaches that the pressure of an acoustical sound wave utilized by Duarte rises regularly to a maximum value above ambient, falls regularly through ambient and on to a minimum value below ambient in a continued oscillation above and below ambient until complete damping occurs. Portions of the wave above ambient represent acoustic compression, while portions below ambient represent acoustic tension.

Senge et al. differentiates an idealized shock wave from the acoustic sound wave of Duarte as having a single pressure spike having a very steep onset, a more gradual relaxation, and virtually no oscillation to produce acoustic tension. Furthermore, Senge et al. teaches that the absence of extensive tension wave components allows the shock wave form to pass through soft tissue to cause controlled trauma within a designated bone sight. Senge et al. also teaches the minimization of the amplitude and extent of tension components in the wave forms for the treatment of bone.

Senge et al. utilizes the extremely short rise time of the shock wave to create high compression zones within bone tissue to cause reactions of the microcompartments of the bone. Senge et al. purports that such reactions cause the formation of hematomas within bone, which in turn, induce the formation of new bone. Senge et al. utilizes a shock wave source consisting of a spark gap between electrodes within a container of water. An electrical condenser connected to the electrodes releases its energy over a very short period of time, and an arc arises between the electrodes of the spark gap device which vaporizes water surrounding the spark's path, establishing a plasma-like state. The result is an explosion-like vaporization of the water which produces an electro-hydraulic shock wave that spreads out in a circular fashion. A metallic, ellipsoid-shaped structure surrounds a rear portion of the spark gap, opposite the patient, to produce a known focal point for positioning within the patient's pathological bone site. This device also requires that the patient be submerged in the water.

Additionally, U.S. Pat. No. 4,979,501 to Valchanov et al., issued on Dec. 25, 1990, teaches a method and apparatus for treating both pathologies with shock or "impact" waves for correction of delayed bone consolidation and bone deformations. The method disclosed in Valchanov et al. comprises the step s of anesthetizing the patient, fixing the limb affected with the pathological bone condition, centering the pathological site of the bone on the shock wave focal point, treating the affected bone site once or consecutively, with 300 to 6000 impacts having a frequency of 0.4–4.0 per second with a pulse duration of 0.5 to 4.0 microseconds for a period of 10–120 minutes, and subsequently immobilizing the limb for a period from 15 to 90 days. The impact wave generating device disclosed by Valchanov et al. generally consists of a vessel which contains a transmitting medium or acoustic liquid such as water contained therein. At a bottom portion of the vessel are opposed electrodes which are adapted to produce a shock across the gap. Therefore, the patient is not submerged for treatment.

Other references teach the treatment of bone pathologies utilizing shock wave therapy in combination with imaging means for localizing the pathology during treatment. Those references include U.S. Pat. Nos. 5,284,144, 5,327,890, 5,393,296, 5,409,446, and 5,419,327. Finally, if the number and magnitude of the shock wave pulses are sufficient, the shock wave treatment may disintegrate a kidney stone. For example, U.S. Pat. No. 4,896,673 to Rose et al., teaches a method and apparatus utilizing focused shock wave treatment of kidney stones in combination with localization using ultrasound or x-ray imaging.

Still other devices utilize transducers for producing ultrasonic waves for therapy of soft tissue. For example, U.S. Pat. No. 5,316,000 to Chapelon et al. teaches an array of composite piezoelectric transducers for making an acoustic or ultrasonic therapy device for use in the treatment of varicose veins. Similarly, U.S. Pat. No. 5,458,130 to Kaufman et al. also purports to therapeutically treat soft tissue such as cartilage, ligament, and tendons using a piezoelectric transducer excited by a composite sine-wave signal with a magnitude as may be prescribed by a physician. Thus, past methods for treating soft tissue surrounding bone utilized a transducer for the generation-of ultrasonic waves for wave propagation into the pathological site within the soft tissue area. Furthermore, as described by Senge et al., clinicians traditionally implemented shock wave therapy for the treatment of bone.

A recent study, reported in "Damage Spinal Cord Found to Have Great Potential for Nerve Regrowth," Case Western Reserve University Press Release, Jul. 15, 1999, describes finding of the capacity for nerve fiber regeneration from transplanted adult nerve cells in adult spinal cords with large lesions. This study implicates molecules in scar tissue at the injury site as the major obstacle to spinal cord regeneration. In the study, sensory nerve cells were transplanted from adult, transgenic mice into the damaged spinal cord of rats, beyond the direct site of the injury. According to current theory, "both normal as well as injured adult white matter tracts in the spinal cord are overtly inhibiting because they contain molecules within the myelin sheaths that signal nerve fibers not to grow." However, instead of seeing a nerve fiber pathway that was inhibitory for nerve growth, the researchers discovered many axons, so that three months later there was still potential for regeneration away from the site of the injury. At the injury site, the researchers found proteoglycan molecules. These molecules have been correlated with the cessation of axon growth. Further, "'not only do the regenerating axons stop upon reaching the scar, but they change the shape of their tips and become 'dystropic' with malformed endings. This is the hallmark of regeneration failure." The researchers concluded that the study indicates that removing or overcoming molecular obstacles in the scar may allow nerve regeneration in the spinal cord.

Therefore, it is an object of the present invention to provide a rapid, time restricted and effective shock wave therapy treatment for pathological conditions that benefit from such treatment. These conditions include, e.g. plantar warts, deep bone bruises, prostate cancer, spinal cord injuries and incontinence. Other objects and features of the present invention will be more readily understood from the following description of the invention.

SUMMARY OF THE INVENTION

This invention relates to methods for medical treatment of pathological conditions. More particularly, the invention relates to methods for using acoustic shock waves to treat a variety of pathological conditions such as plantar warts, deep bone bruises, prostate cancer, benign prostatic hypertrophy, incontinence and the treatment of spinal cord injuries, including the reduction or removal of scar tissue lo aid in spinal cord regrowth. In particular, this invention may be used to remove or reduce scar tissue in the spinal cord, thereby permitting nerve generation, and may be used in conjunction with therapy described above for spinal cord injury.

This invention relates to a method of treating a pathological condition by applying a sufficient number of acoustic shock waves to the site of a pathological condition to induce or accelerate healing in a patient in need thereof. Applying the acoustic shock waves involves generating about 400 to about 3000 acoustic shock waves by applying a voltage potential across a spark gap of a spark gap generator ranging from about 14 kV to about 28 kV to generate each shock wave. The acoustic shock waves may be applied either in a single treatment or in multiple treatments.

In a particular embodiment, the pathological condition is treated by locating a site or suspected site of the pathological condition in a patient in need thereof, generating acoustic shock waves, focusing the acoustic shock waves on the located site, and applying a sufficient number of acoustic shock waves to the located site to induce or accelerate healing. Generating the acoustic shock waves involves generating about 400 to about 3000 acoustic shock waves by applying a voltage potential across a spark gap of a spark gap generator ranging from about 14 kV to about 28 kV to generate each shock wave.

The pathological conditions treated may include deep bone bruises, scar tissue in the spinal cord, incontinence, plantar warts, prostate cancer, or benign prostatic hypertrophy.

The method according to particular embodiments of the invention may utilize physical palpation, X-ray image intensification, CT direction, or ultrasonography precisely to locate the pathological site. Once the site is located, the inventive method may utilize an ellipsoid reflector or focusing lens specifically to direct the acoustic shock waves to the impact (treatment) site.

BRIEF DESCRIPTION OF THE DRAWINGS

FIG. 1 is a schematic representation of a shock wave generation device with a focusing mechanism used in accordance with the inventive method.

FIGS. 4 and 5 illustrate schematic representations of monitors that display images of alignment targets for the therapy head in unaligned and aligned positions, respectively.

DETAILED DESCRIPTION OF SPECIFIC EMBODIMENTS

Implementation of the method of the present invention requires the use of a locating device or palpation to locate the pathological site. Locating devices may include, but are not limited to X-ray or ultrasound machines. For example, the method and apparatus described in U.S. Pat. No. 4,896, 673 to Rose et al., issued Jan. 30, 1990, the disclosure of which is incorporated herein in its entirety, may be used according to this invention locate the pathological site.

The method also typically requires a shock wave source, such as a spark gap generator. Suitable spark gap generators are d Described in U.S. Pat. No. 4,905,671 to Senge et al.; U.S. Pat. No. 4,979,501 to Valchanov et al.; U.S. Pat. No. 5,284,143 to Rattner; U.S. Pat. No. 5,327,890 to Matura et al.; U.S. Pat. No. 5,393,296 to Rattner; U.S. Pat. No. 5,409,446 to Rattner; and U.S. Pat. No. 5,419,327 to Rohwedder et al., the disclosures of which are hereby incorporated by reference. The method according to the present invention may also utilize the electromagnetic shock wave source and parabolic wave focusing means of the type described in U.S. Pat. No. 5,327,890 to Matura et al., the disclosure of which is hereby incorporated by reference. The focusing means may also comprise parabolic reflectors utilized in kidney lithotripters.

The method typically requires use of apparatus for focusing the acoustic shock waves with an appropriate device, such as an ellipsoid or parabolic focusing lens. The reflector is generally located in a therapy head, which directs the waves to a focal point. FIG. 1 is a schematic representation of such a shock wave generator and focusing means. Shock waves 4 radiate from electrode 9 and through water (not shown). Waves 4 reflect from ellipsoid surface 8 and toward focal point 10.

Figure 2:
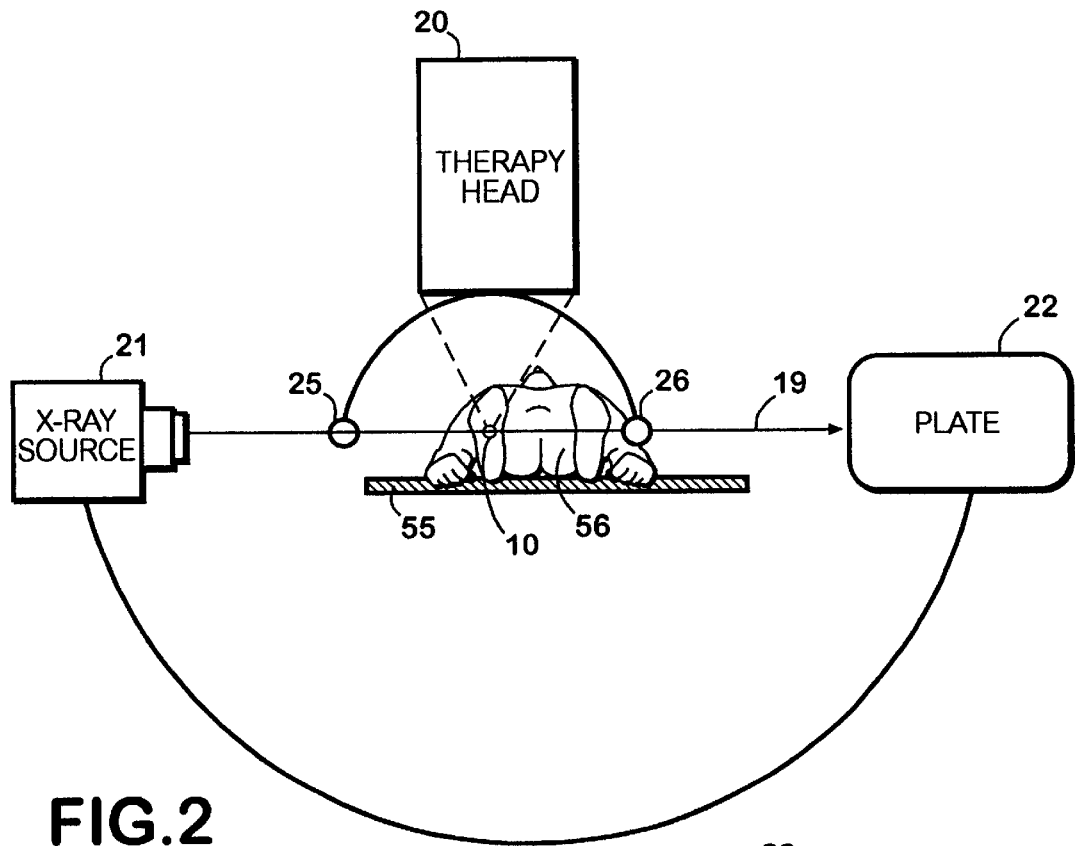
FIG. 2 is a schematic representation of a therapy head and locating mechanism used in accordance with the inventive method.
Figure 3:
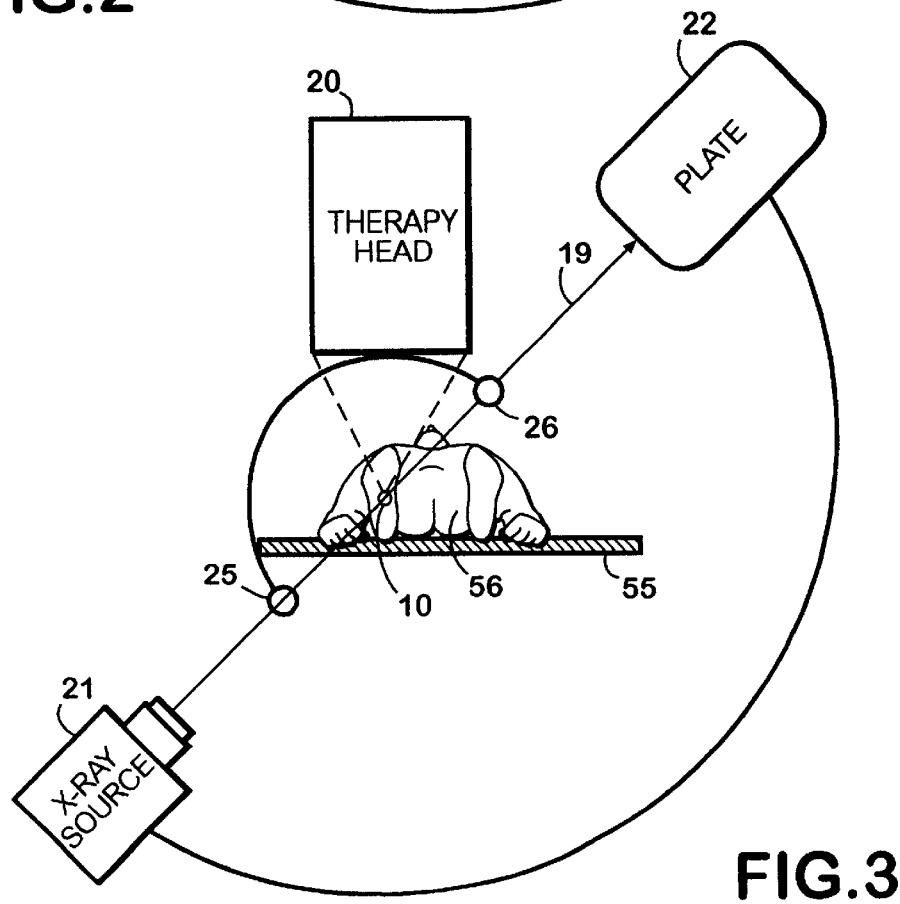
FIG. 3 is a schematic representation of the therapy head and locating mechanism illustrated in FIG. 2 with the locating mechanism orientated at a 45 degree angle with respect to a horizontal plane.

In a preferred embodiment, the therapy head also includes a targeting device which functions in conjunction with an X-ray machine locating device, as is illustrated in FIGS. 2 and 3 or other appropriate locating device. FIGS. 2 and 3 schematically illustrate a patient 56 positioned on a surface 55 during a treatment session. Two movable targets 25 and 26 are connected mechanically to the therapy head 20 so that the pair of targets 25 and 26 may rotate around at least two different axes with an imaginary connecting line 19. An X-ray source 21 and plate 22 define a connecting line 19 which passes through the targets 25 and 26. Connecting line 19 always extends between the two targets and throughout the focal point 10 of the shock waves. Before beginning treatment in accordance with the present invention, the clinician aligns the tissue area to be treated with the approximate center of an X-ray image being projected by the source 21. An appropriate monitor 29 illustrates the projection of the X-ray image as illustrated in FIGS. 4 and 5. As illustrated in FIG. 4, when targets 25 and 26 do not coincide with one another, then focal point is not aligned with the treatment site 2. After proper alignment, as shown in FIG. 5, the targets 25 and 26 coincide with the treatment site, and the clinician may begin treatment. As illustrated in FIG. 3, the imaging mechanism may also be, positioned at various angles with respect to the patient depending on the location of the treatment site within the patient. Alternatively, an ultrasound locating unit positions the shock wave focal point between the patient's pathological site and the acoustically reflective object.

While we do not wish to be bound by the following explanation, we believe it describes the manner in which the invention induces or accelerates healing. The present invention comprises a method of applying acoustical shock waves to the site of a pathological condition to induce, reactivate or accelerate the body's natural healing processes, especially through natural cellular and molecular (macromolecular) biologic responses, including the stimulation of tissue specific group factors (cytokines, morphogenetic proteins), to improve local microcirculation through activated neoangiogenesis, and to disrupt scar tissue to enhance ingrowth or through growth of normal tissue components, especially cells and cellular extensions, thereby reestablishing normal tissue morphology and function. The method according to the present invention may also include the steps of locating the site of a pathological condition, generating acoustic shock waves, focusing the acoustic shock waves on the pathological site, and applying the focused acoustical shock waves on the site to induce localized trauma and various tissue and cellular responses, such as cellular apoptosis, micro-fractures, as well as to induce osteoblastic responses such as cellular recruitment, stimulate formation of molecular bone, cartilage, tendons, fascia and soft tissue morphogens and growth factors, and to induce vascular neoangiogenisis. This method may also include the step of freezing the tissue to be treated prior to treatment. The method similarly induces neoangiogenesis and the formation, recruitment or stimulation of tissue specific morphogenetic macromolecules and growth factors.

Micro-disruptions resulting from the shock wave therapy are believed to induce cellular changes, and extracellular matrix and macromolecular changes in a controlled fashion for the purpose of stimulating increased neoangiogenesis, leading to adequate tissue vascularization. The increased circulation and vascutlarization then induce the body's natural cellular (tissue specific) healing processes. The accompanying cellular changes lead to or are associated with elaboration and production of bone and tissue morphogenetic proteins, known as growth factors. The accompanying cellular changes may also lead to a dampening or reversal of abnormal cellular reactivity, especially at the molecular level.

Particular applications of the method are illustrated in the following examples.

The inventive method may include a wide range in the various parameters used to treat all of the pathologies mentioned in this specification. Specifically, for each of the pathologies mentioned in this specification, the inventive method may include applying a range of approximately 14–28 kilovolts of energy per pulse; the pulse frequency may be approximately 0.5–5 Hz (pulses/sec) and the pulse duration may be approximately 280 ns. The number of pulses per treatment should be approximately 500–10,000, and the total time per treatment should be approximately 5 minutes to 2 hours. Additionally, the number of treatments necessary for a positive response may vary from 1 to 3.

The inventive method may be used in the treatment of urinary incontence using the parameters set forth above. Application of transcutaneous high energy shock waves to the periurethral tissues will result in neovascularzation and the generation of new, healthy tissue in the urethral vesical junction and adjoining areas. This will cause the bladder to be drawn up and the urethal angle to be properly restored. Additionally, application of shock waves to scarred or damaged sphincter tissue will revascularize and regenerate the damaged tissue resulting in improved function of the sphincter.

The inventive method may also be used to induce the generation of nerve cells in spinal cord injuries. In a preferred embodiment, about 800 to about 4000 acoustic shock waves are generated by applying a voltage potential across a spark gap generator ranging from about 14 kV to about 28 kV to generate each shock wave. These shock waves are applied to the area where nerve celll generation is desired in one or more treatments. Additionally, scarring following spinal, cord transection may be treated and reduced by applying a sufficient number of acoustic shock waves specifically to scar tissue. First, the scar tissue is located in the patient by magnetic resonance imaging and/or gadolinium CT scanning. About 2000 to about 6000 acoustic shock waves are generated by applying a voltage potential across a spark gap of a spark gap generator ranging from about 14 kV to about 28 kV to generate each shock wave. These shock waves are applied to the scar tissue in one or more treatments.

This invention may also be used in the treatment of prostate cancer or benign prostatic hypertrophy. The acoustic impedance of a material is equivalent to the speed of sound multiplied by density. In using acoustic shock waves on soft tissue, the acoustic impedance is lower than it is when treating bone. In other words, bone is harder than tissue so that energy is immediately released on contact with bone. In order to better treat soft tissue, such as in the case of prostate cancer treatment, the tissue to be treated may be frozen and then treated with shock waves. This process of freezing the tissue prior to application of the acoustic shock waves renders the tissue harder, thereby increasing the acoustic impedance, making the tissue easier to break up and destroy.

Current freezing techniques that would be suitable in the treatment of prostate cancer include insertion of a probe or needle having a sheath into the tissue, and pumping cooling fluid down through the probe or needle and into the tissue. Alternatively, freezing may be accomplished trans-urethrally or by needle biopsy.

After the tissue to be treated has been frozen it may be treated by applying a sufficient number of acoustic shock waves to the tissue. First, the tissue is located in the patient. About 2000 to about 6000 acoustic shock waves are generated by applying a voltage potential across a spark gap of a spark gap generator ranging from about 14 kV to about 28 kV to generate each shock wave. These shock waves are applied to the tissue in one or more adjuvant treatments.

While the invention has been described in terms of various preferred embodiments, those of skill in the art will appreciate that various modifications, substitutions, omissions and changes may be made without departing from the spirit thereof. Accordingly, it is intended that the scope of the present invention not be limited solely by the scope of the claims.

We claim:

1. A method of treating scar tissue in the spinal cord comprising:

locating a site or suspected site of a pathological condition associated with said scar tissue;

generating acoustic shock waves;

focusing said acoustic shock waves on the located site; and applying a sufficient number of acoustic shock waves to the located site to induce or accelerate healing.

2. The method of claim 1, wherein generating acoustic shock waves comprises generating about 2000 to about 6000 acoustic shock waves by applying a voltage potential across a spark gap of a spark gap generator ranging from about 14 kV to about 28 kV to generate each shock wave.

3. The method of claim 1, wherein said applying a sufficient number of acoustic shock waves comprises applying the generated acoustic shock waves in a single treatment.

4. The method of claim 1 wherein the acoustic shock waves are focused on the located site with an ellipsoid reflector, and wherein applying the acoustic.

5. A method for inducing or accelerating the generation of nerve cells in the treatment of a spinal cord injury comprising:

locating a site or suspected site of a pathological condition associated with the spinal cord injury;

generating acoustic shock waves;

focusing the acoustic shock waves on the located site; and applying a sufficient number of acoustic shock waves to the located site to induce micro-injury and increased vascularization thereby inducing or accelerating the generation of nerve cells.

6. The method of claim 5, wherein said generating acoustic shock waves comprises generating about 800 to about 4000 acoustic shock waves by applying a voltage potential across a spark gap of a spark gap generator ranging from about 14 kV to about 28 kV to generate each shock wave.

7. The method of claim 5, wherein said applying a sufficient number of acoustic shock waves comprises applying the generated acoustic shock waves in a single treatment.

8. The method of claim 5, wherein the acoustic shock waves are focused on the located site with an ellipsoid reflector.

* * * * *

UNITED STATES PATENT AND TRADEMARK OFFICE
CERTIFICATE OF CORRECTION

PATENT NO. : 6,368,292 B1
DATED : April 9, 2002
INVENTOR(S) : John A. Ogden

It is certified that error appears in the above-identified patent and that said Letters Patent is hereby corrected as shown below:

Column 5,
Line 27, delete "2"

Column 6,
Line 44, delete "spinal, cord" and substitute -- spinal cord --

Column 8,
Line 9, delete ", and wherein applying the acoustic"

Signed and Sealed this

Seventeenth Day of September, 2002

Attest:

JAMES E. ROGAN
Attesting Officer
Director of the United States Patent and Trademark Office

UNITED STATES PATENT AND TRADEMARK OFFICE
CERTIFICATE OF CORRECTION

PATENT NO. : 6,368,292 B1  
DATED : April 9, 2002  
INVENTOR(S) : John A. Ogden

It is certified that error appears in the above-identified patent and that said Letters Patent is hereby corrected as shown below:

<u>Title page,</u>
Item [75], Inventors, delete "John F. Warlick, Woodstock, both of" and substitute -- , --

Signed and Sealed this

Seventeenth Day of May, 2003

JAMES E. ROGAN
*Director of the United States Patent and Trademark Office*